United States Patent [19]

Lantero et al.

[11] Patent Number: 5,231,017
[45] Date of Patent: Jul. 27, 1993

[54] PROCESS FOR PRODUCING ETHANOL

[75] Inventors: Oreste J. Lantero, Goshen; John J. Fish, Bremen, both of Ind.

[73] Assignee: Solvay Enzymes, Inc., Elkhart, Ind.

[21] Appl. No.: 701,871

[22] Filed: May 17, 1991

[51] Int. Cl.$^5$ .................. C12P 7/06; C12P 7/14; C12N 9/62; C12N 9/30
[52] U.S. Cl. .................. 435/161; 426/11; 426/26; 426/29; 435/93; 435/162; 435/163; 435/165; 435/225
[58] Field of Search .......... 435/161, 163, 162, 165, 435/225, 93; 426/11, 16, 29; 425/225

[56] References Cited

U.S. PATENT DOCUMENTS

| | | | |
|---|---|---|---|
| 3,623,957 | 11/1971 | Feldman | 435/222 |
| 3,880,742 | 4/1975 | James et al. | 435/200 |
| 4,016,038 | 4/1977 | Sugimoto et al. | 435/95 |
| 4,092,434 | 5/1978 | Yoshizumi et al. | 435/93 |
| 4,241,183 | 12/1980 | Witt et al. | 435/95 |
| 4,514,496 | 4/1985 | Yoshizumi et al. | 435/161 |
| 4,532,213 | 7/1985 | Shetty et al. | 435/225 |
| 4,933,279 | 6/1990 | O'Carroll et al. | 435/99 |

FOREIGN PATENT DOCUMENTS

| | | |
|---|---|---|
| 1143677 | 3/1983 | Canada . |
| 0131563 | 1/1985 | European Pat. Off. ............. 435/93 |

OTHER PUBLICATIONS

Mullins et al "Biomass" 16 (1988) 2, pp. 77-87.
Mullins et al Biotech Abs 90:07744 "Energy Biomass Wastes" (1988) 931-51.
J. T. Mullins & C. NeSmith, "Biomass" 16 (1988) pp. 77-87.

Primary Examiner—Herbert J. Lilling
Attorney, Agent, or Firm—Willian Brinks Olds Hofer Gilson & Lione

[57] ABSTRACT

The invention relates to a process for producing ethanol from raw materials, that contain fermentable sugars or constituents which can be converted into sugars, comprising the steps of:

a-liquefaction of the raw materials in the presence of an alpha-amylase for obtaining liquefied mash, b-saccharification of the liquefied mash in the presence of a glucoamylase for obtaining hydrolyzed starch and sugars, c-fermentation of the hydrolyzed starch and sugars by yeast for obtaining ethanol, and d-recovering alcohol, a protease being introduced in the liquefied mash during the saccharification and/or in the hydrolyzed starch and sugars during the fermentation.

The invention relates also to a composition containing a glucoamylase and an acid fungal protease.

11 Claims, No Drawings

PROCESS FOR PRODUCING ETHANOL

BACKGROUND OF THE INVENTION

1. Field of the Invention

The invention relates to a process for producing ethanol.

2. Description of Related Art

The process for producing ethanol from fermentation of whole grain mashes is well known.

The addition of alkaline protease enzymes to mash has been shown in Biomass 16 (1988) 77–87 to increase amino nitrogen sufficient to support accelerated rates of ethanol fermentation: the addition of a protease, an alkaline protease derived from *Streptomyces griseus*, to sorghum or milo mash resulted in higher ethanol fermentation rates.

Canadian Patent 1 143 677 describes a process for producing ethanol form amylaceous raw stock, such as wheat, barley or rye. This process comprises a step of hydrolyzing starch, cellulose and some other substances contained in corn grains in the presence of a complex hydrolytic enzyme produced by a fungi *Trichoderma koningii*, and containing $C_1$-enzyme, endo- and exo-glucanase, cellobiase, xylanase, beat-glucosidase, protease, and a number of amylolytic enzymes.

However these processes do not allow the production of ethanol when a higher dry solids mash level is present in the fermenter.

SUMMARY OF THE INVENTION

The object of the present invention is to provide a process wherein the rate of ethanol production is increased and in which yeast can ferment mash in the presence of a higher dry solids mash level in the fermenter and obtain higher ethanol levels.

Another important advantage of the invention is that the thin stillage obtained from fermenters according to the process of the present invention is less viscous than the thin stillage from fermenters according to known processes at the same dry solids level. In practice this may help reduce fouling in the evaporator and/or allow one to evaporate the thin stillage at higher levels of solids. Also one would expect the less viscous stillage to blend easier with the spent grains prior to drying.

The present invention relates to a process for producing ethanol from raw materials containing a high dry solids mash level, and that contain fermentable sugars or constituents which can be converted into sugars, comprising the steps of:

a-liquefaction of the raw materials in the presence of an alpha-amylase to obtain liquefied mash, b-saccharification of the liquefied mash in the presence of a glucoamylase to obtain hydrolysed starch and sugars.

c-fermentation of the hydrolysed starch and sugars by yeast to obtain ethanol and d-recovering the ethanol, wherein a protease is introduced to the liquefied mash during saccharification and/or to the hydrolysed starch and sugars during the fermentation.

More preferably the protease is a fungal protease. Good results have been obtained with an acid fungal protease.

DETAILED DESCRIPTION OF PREFERRED EMBODIMENTS

The proteases used in the process can be from microbial, plant and/or animal origin and are characterized by their ability to hydrolyse proteins under acidic conditions.

Mixtures of proteases can also be used.

As examples of proteases are the bacterial proteases of *Bacillus licheniformis*, *Bacillus subtilis*, *Bacillus cereus* or *Streptomyces fradiae* plant proteases such as papain, bromelain or ficin, fungal proteases, such yeast proteases as *Candida albirans* or animal proteases such as pepsin or chymosin.

The acid fungal protease used in the process according to the invention is an acid protease produced by fungi, and is characterized by its ability hydrolyze proteins under acidic conditions. Generally the acid fungal protease is derived from Aspergillus, Mucor, Rhizopus, Candida, Coriolus, Endothia, Enthomophtora, Irpex, Penicillium, Sclerotium and Torulopsis. Usually the acid fungal protease chosen is thermally stable and is derived from Aspergillus, such as *A. niger*, *A. saitoi* or *A. oryzae*, from Mucor such as *M. pusillus* or *M. miehei*, from Endothia, such as *E. parasitica*, or from Rhizopus, such as R. spp. Preferably the acid fungal protease is derived from *Aspergillus niger*. More particular preference is afforded to the acid fungal protease from *Aspergillus niger*, var., known under the trade mark AFP-2000, available through Solvay Enzymes, Inc.

The quantity of the acid fungal protease used in the process according to the invention depends on the enzymatic activity of the protease. Generally an amount between 0.001 and 2.0 ml of a 2% solution of the acid fungal protease is added to 450 gm of a slurry adjusted to 20–33% dry solids, the slurry being the liquefied mash during the saccharification and/or in the hydrolysed starch and sugars during the fermentation. Usually it is added in an amount between 0.005 and 1.5 ml of such a solution. Preferably it is added in an amount between 0.01 and 1.0 ml of such a solution.

The alpha-amylase used in the process according to the invention is generally an enzyme which effects random cleavage of alpha-(1-4) glucosidic linkages in starch. Usually the alpha-amylase is chosen from among the microbial enzymes. These enzymes have an E. C. number E. C. 3.2.1.1 and in particular E. C. 3.2.1.1-3. Preferably the alpha-amylase used in the process according to the invention is chosen amongst the thermostable bacterial alpha-amylases. More particular preference is afforded to alpha-amylase derived from Bacillus. Good results have been obtained with the alpha-amylase derived from *Bacillus licheniformis* commercially available from Solvay Enzymes, Inc. under the trademark TAKA-THERM II.

The quantity of alpha-amylase used in the process according to the invention depends on the enzymatic activity of the alpha-amylase. Generally an amount between 0.001 and 2.0 ml of a solution of the alpha-amylase is added to 1000 gm of raw materials. Usually it is added in an amount between 0.005 and 1.5 ml of such a solution. Preferably it is added in an amount between 0.1 and 1.0 ml of such a solution.

The glucoamylase used in the process according to the invention is generally an enzyme which removes successive glucose units from the non-reducing ends of starch. It can hydrolyze both the linear and branched glucosidic linkages of starch, amylose and amylopectin.

Usually the glucoamylase is chosen from among the microbial enzymes. Preferably the glucoamylase used in the process according to the invention is chosen from among the thermostable fungal glucoamylases. More particular reference is afforded to glucoamylase derived from Aspergillus. Good results have been obtained with the glucoamylase derived from *Aspergillus niger* commercially available from Solvay Enzymes, Inc. under the trademark DISTILLASE.

The quantity of glucoamylase used in the process according to the invention depends on the enzymatic activity of the glucoamylase. Generally an amount between 0.001 and 2.0 ml of a solution of the glucoamylase is added to 450 gm of a slurry adjusted to 20-30% dry solids, the slurry being the liquefied mash during the saccharification and/or in the hydrolysed starch and sugars during the fermentation. Usually it is added in an amount between 0.005 and 1.5 ml of such a solution. Preferably it is added in an amount between 0.01 and 1.0 ml of such a solution.

The yeast used in the process according to the invention is generally baker's yeast, also known as ascomycetous yeast or *Saccharomyces cerevisiae*. Good results have been obtained with Fleishmanns's bakers yeast.

The raw materials that contain fermentable sugars or constituents which can be converted into sugars are usually starch-containing raw materials, such as tubers, roots, whole ground corns, cobs, grains, wheat, barley, rye, milo or cereals, sugar-containing raw materials, such as molasses, fruit materials, sugar cane or sugar beet, cellulose-containing materials, such as wood or plant residues. The raw materials are preferably starch-containing raw materials such as cobs, whole ground corns, corns, grains, milo or cereals and mixtures thereof. Good results have been obtained with cobs, corns or milo and their mixtures.

The steps of liquefaction, saccharification, fermentation and recovering ethanol are well known. For example these steps are described in Fundamentals of Biotechnology edited by P. Präve, U. Faust, W. Sittig, D. A. Sukatsch, 1987, chapter 10, pages 381-403, incorporated herein by reference.

The saccharification and the fermentation steps are carried out either simultaneously or separately. Preferably the saccharification and the fermentation steps are carried out simultaneously. When carried out simultaneously the glucoamylase and the acid fungal protease can be introduced as a single mixture composition or. Such a composition, containing the glucoamylase derived from *Aspergillus niger* (trade mark DISTILLASE) and the acid fungal protease derived from *Aspergillus niger* (trade mark AFP-2000) is sold under the trade mark FERMENZYME by Solvay Enzymes, Inc.

It may also be advantageous to add some nutrients, to the liquefied mash during saccharification and/or add nutrients to the hydrolysed starch during fermentation. Examples of such nutrients are backset, yeast extract, corn steep liquor and mixtures thereof.

It may also be advantageous to add some salts to the liquefied mash during saccharification and/or to add salts to the hydrolysed starch and sugars during fermentation. Examples of such salts are NaCl and ammonium sulfate.

It may also be advantageous to add some other enzymes to the liquefied mash during saccharification and/or to add the enzymes to the hydrolysed starch and sugars during fermentation. Examples of such enzymes are cellulases, hemicellulase, phosphatase, exo- and endoglucanases, and xylanase.

Generally, in the fermentation of whole grain mashes, the ethanol is recovered by distillation. The remaining stillage is centrifuged to remove the spent grain solids form the thin stillage. The thin stillage reaction is then concentrated to a syrup consisting of about 30-45% solids. The syrup is then combined with the spent grain fraction and dried, resulting in distillers dry grain solids plus solubles (DDGS plus solubles). The DDGS plus solubles is sold for animal feed. During the concentration of the thin stillage, evaporator fouling is quite common, and periodically the evaporator must be cleaned. Another problem with concentrating the thin stillage is that at 30-40% solids the viscosity is very high. On cooling, the syrup usually forms a gel. It seems reasonable that the gelling may be due to protein and starch. The presence of starch could be substituted to incomplete liquefication of the ground corn slurry, and that during distillation some liquefication of starch may occur.

By the use of the acid fungal protease according to the invention, mash with a higher level of dry solids can be fermented to obtain higher levels of ethanol. The addition of acid fungal protease added to grain mash allows ethanol fermentation by yeast in the presence of higher dry solids mash levels.

EXAMPLE 1

This example demonstrates how the presence of acid fungal protease (AFP) improves the rate of ethanol formed and the level of ethanol achieved by yeast fermentation of whole corn mash.

Step a: Liquefaction

The first step is the liquefaction of the whole corn. Ground whole corn can be obtained from a commercial fuel alcohol producer. For liquefaction, 1740 gm of ground corn is added to 4500 ml of tap water. To this slurry is added 0.99 gm of $CaCl_2.2H_2O$. The slurry is then placed in 68° C. water bath, and the pH adjusted to 6.2-6.4. Then, while constantly stirring, 0.6 ml of the enzyme Taka-Therm® II is added to the slurry and then incubated at 68° C. for one hour. The enzyme Taka-Therm® II is a liquid thermal stable bacterial (*Bacillus licheniformis* var.) alpha-amylase commercially available from Solvay Enzymes, Inc. No noticeable gelatinization is observed during the incubation. The slurry is then placed on a hot plate and brought to a boil with agitation of the slurry. The slurry is boiled for five minutes and then placed in 90° C. water and incubated for two hours. After the boil, an additional 1.2 ml of the enzyme Taka-Therm® II is added to the slurry. The slurry is cooled to 25° C. and the pH adjusted to 4.6-4.8 with 25% $H_2SO_4$. The dry solid level (DS) is adjusted to 20-21% with tap water.

Step b: Saccharification and Fermentation

The saccharification and fermentation are carried out simultaneously in 500 ml Erlenmeyer flasks by adding 450 gm of the liquefied corn mash obtained in step a (liquefaction). The appropriate amount of enzymes, as shown in table 1, is then added to the mash along with 0.8 gm of Fleishmann's bakers yeast (7 gm foil package). The dry yeast is allowed to hydrate by about 10 minutes prior to swirling the flasks to mix in the yeast. The flasks are then covered with Parafilm and placed in a 36° C. water to allow fermentation for an appropriate time. Periodically, a 10 ml sample is withdrawn from the flask for analysis.

Analysis

Routinely, samples are taken and the pH measured. The alcohol and carbohydrate levels are estimated by HPLC. Prior to HPLC analysis, the samples are centrifuged and the supernatant appropriately diluted (10 fold dilution) with 0.01N $H_2SO_4$ and filtered through a 0.45 $\mu$ filter. A 20 $\mu$l sample is used for separation on BioRad HPX 87H column at 60° C. using as mobile phase 0.01N $NH_2SO_4$ at a flow rate of 0.7 ml/min. The detector is a refractive index detector and peak areas are used for quantitation. The carbohydrates are given as % w/v DS by using a glucose standard. Glycerol and lactic acid are similarly expressed as % w/v using standards of glycerol and lactic acid. Ethanol is reported in % v/v using ethanol standards.

Results

For this example, 0.267 ml of the enzyme Distillase ® L-200 is added per flask. The enzyme Distillase ® is the trade name of liquid glucoamylase (AG) derived from *Aspergillus niger* var. (which can be obtained from Solvay Enzymes, Inc.) containing 200 Diazyme units per ml. As shown in Table 1, varying amount of acid fungal protease, (a 2% solution of the enzyme AFP-2000) is added per flask. The enzyme AFP-2000 is an acid fungal protease from *Aspergillus niger* var. available through Solvay Enzymes, Inc.

Table 1 summarizes the results obtained from the simultaneous saccharification and fermentation of whole corn mash with the addition of acid fungal protease (AFP). The results show the addition of AFP increased the rate and level of ethanol obtained. These results show about a 12% increase in ethanol. The increase in ethanol yield can be seen to be the result or more complete fermentation. Without AFP present, more glucose remains unfermented.

The glycerol level is approximately the same with or without AFP present. If one considers the ethanol produced, the glycerol level is substantially less where the fermentations contain protease. There is slightly less pH drop with protease present in the fermenter as well. The lactic acid levels are not shown, but in all cases, the lactic acid level is less than 0.1%.

The results also show that increasing the amount of glucoamylase increased that rate of saccharification as noted by the lower amount of non-fermentable sugars and increased glucose early in the fermentation. Increased levels of glucose do not increase the rate of ethanol formation. It would appear the fermentation rate is not limited by fermentable carbohydrates.

EXAMPLE 2

Whole corn mash is prepared according to the process given in Example 1 with the amount of yeast added varied at 0.8 or 1.6 gm Fleishmann's yeast per flask. Also, for this example, three levels of protease (acid fungal protease) are investigated. The fermentation procedure and sampling is similar to that given in Example 1. The results are given in Table 2.

The higher level of yeast (1.6 gm) seemed to result in an increased fermentation rate that essentially reduced the fermentable sugar (glucose and maltose) levels to the extent of reducing the viability of the yeast. In all cases, the alcohol yield is not as high as with the lower yeast level (0.8 gm). At the 0.8 gm yeast level, the addition of protease gives similar results as in Example 1 i.e., faster fermentation, a higher level of ethanol and more complete fermentation of the fermentable sugars.

EXAMPLE 3

In this example, whole corn mash is fortified with yeast. The influence extract of AFP is also investigated. The yeast extract used for this example is known under trademark Amberex 1003 from Universal Foods Corp., Milwaukee, Wis. The yeast extract Amberex 1003 is a water soluble brewers yeast extract produced by the autolytic action of yeast proteases. It contains proteins, peptides, free amino acids, vitamins, minerals and trace elements. The protein content (Nx6.25) is 56% with a high amount of free amino nitrogen as indicated by the amino nitrogen to total nitrogen ratio of 30.

The liquefaction of whole corn is conducted as in Example 1, and 450 gm of 20% DS liquefied mash is added per flask. The other additives are given in Table 3 and the fermentation is carried out at 33° C. Samples are removed from the fermenters and treated as described in Example 1. Table 3 summarizes only the ethanol levels during the fermentations.

The addition of yeast extract is shown to increase the rate of ethanol production during the fermentation (Table 3). The addition of AFP along with yeast extract gives an increased ethanol yield up to the high level of yeast extract (16 ml/flask). These results give evidence that the protease probably is producing amino nitrogen from the grain protein that is readily metabolized by the yeast.

EXAMPLE 4

Generally, in commercial fuel alcohol production, the liquefied whole corn mash is diluted with thin stillage, commonly referred to as backset, prior to fermentation. The addition of backset accomplishes two main objectives, it adds nutrients to the mash and also reduces the volume of thin stillage to be concentrated. In this example, whole corn mash is obtained from a fuel alcohol producer to evaluate the role of acid fungal protease on the fermentation. The commercial mash used for this example is already liquefied and contains the normal dosage of glucoamylase and backset, diluted to the normal level of solids inoculated with yeast. The only variable is the addition of acid fungal protease. Each flask contains 450 gm of the mash and the amount of AFP shown in Table 4. The flask are then placed in a 30° C. water bath for fermentation. The fermentation performance is monitored by HPLC as described in Example 1 and summarized in Table 4.

The results in Table 4 show similar type of benefits with AFP in mash containing backset as shown earlier using only whole corn mash (no backset), i.e., fast ethanol formation and higher yield of ethanol.

EXAMPLE 5

Prior examples have shown that fermentation with acid fungal protease added to the mash increased the rate and yield of ethanol. The fermentations were essentially conducted with mash at the same concentration of dry solids (DS). In this example, whole corn mash is fermented at various mash DS levels with and without acid fungal protease added. Commercial liquefied whole corn is diluted with tap water to various levels. At each DS level DS, the corresponding enzymes and dry yeast are added as shown in Table 5. The mash DS level is determined by drying a sample overnight in a forced air oven at 100° C. The fermentations are conducted at 33° C. and sampling conducted as described in Example 1. The results are summarized in Table 5.

The ethanol results are further summarized in Table 6. At each mash level, the results show that the addition of protease increased both the rate of ethanol formed and the yield of ethanol. The results also show that only with the presence of the protease could 15% v/v ethanol be achieved. It appears that maximum ethanol production is achieved at about 28% DS mash solid while still obtaining complete fermentation.

EXAMPLE 6

Example 5 shows that whole grain fermented with acid fungal protease present, increased the rate of ethanol formed and the level of ethanol reached (15% v/v). This example shows the response of acid fungal protease at various dry solid mash levels containing thin stillage. Commercial liquefied whole corn is combined with thin stillage concentrate at a constant ratio so that 8.6% of the total solids is from thin stillage.

The fermentation conditions are similar to those given in Example 5, and are summarized in Table 7 along with the fermentation results. The presence of the protease (AFP) again increased the rate of ethanol fermentation as well as the level of ethanol related relative to the control flasks which contain no protease.

EXAMPLE 7

This example illustrates the effectiveness of AFP during saccharification. The main difference during the separate steps of saccharification and fermentation is that during the saccharification, the temperature is significantly higher than the fermentation temperature. Generally, saccharification is carried out at 60° C. Whole corn mash is liquefied as in Example 1. The liquefied mash is then treated by two different methods. In one case (A), 450 gm of mash is transferred to the flask and the appropriate amount of AG and AFP (Shown in Table 8-A) are added and then placed in a 60° C. water bath for 24 hours allow saccharification. After saccharification, the flasks are cooled to 25° C. and inoculated with dry yeast and placed in a 33° C. water bath for fermentation. For the second case (B), liquefied mash is transferred to flasks similar to A, only AG is added and the flasks are incubated at 60° C. for 24 hours. Then the flask are cooled and the appropriate amounts of protease (AFP) and yeast are added, and placed in a 33° C. water bath for fermentation. Progress of the fermentation is monitored by HPLC analysis as described in Example 1.

Table 8-A summarizes the results of the action of AFP during both high temperature saccharification and fermentation. These results show that AFP is able to hydrolyze protein at the saccharification temperature. It's presumed that since AFP is present during saccharification, the protease is active and is digesting the protein. AFP is also present during fermentation and could also have been actively hydrolyzing protein at that stage. Post saccharification addition of AFP (Part B) results in the same increased fermentation rate as seen in earlier example with AFP. The levels of ethanol present at various times fermentation for both parts of the example are summarized in Table 9. The results also show that excess AFP does not seem to give any added benefit in increasing the fermentation rate.

These results show that the AFP activity is stable enough to be effective at 60° C. This is important for instances where some saccharification is carried out prior to fermentation. These results suggest that AFP and AG can be a mixture added as such whether saccharification and fermentation are separate or simultaneous.

EXAMPLE 8

Corn is the most widely used starch source to ferment into ethanol in the U.S. Milo is probably the next used starch source. In this example, whole grain milo is used to evaluate the influence of AFP for fermentation into ethanol. Whole ground milo is slurried and liquefied by the same procedure in Example 1 for whole ground corn. The conditions for fermentation in Example 1 are also used i.e., 450 gm of 20% DS mash per flask. The simultaneous saccharification/fermentation conditions are similar to Example 1. The enzyme levels are given in Table 10. The results show that the rate of ethanol formation is greater when AFP is present, a result similar to corn mash fermentation with AFP. These results suggest that AFP can convert proteins in milo into amino nitrogen that readily metabolized by the yeast.

EXAMPLE 9

In this example, concentrated thin stillage obtained from a commercial fuel alcohol producer is treated with glucoamylase (Distillase) and AFP to try and reduce the viscosity of the syrup. The thick syrup is diluted with water to 14.7% DS. Three samples of the diluted syrup are incubated at 36° C. overnight: 1) Control, 2) Distillase containing, and 3) AFP containing. After the incubation, the samples are concentrated in a rotary evaporator to 30% DS, and the viscosity if measured using a Brookfield Viscometer, Model RVF/100 at 25° C. The control had a viscosity of 1455 cps and the AG and AFP sample had viscosities of 835 and 668 cps respectively. These results show that both protease and carbohydrate material contribute to viscosity. It follows then that AFP added to the mash should help reduce the viscosity of thin stillage and possibly reduce evaporator fouling.

EXAMPLE 10

This example illustrates the property of AFP to reduce the viscosity of the thin stillage when added to the whole grain mash. Commercial liquefied corn mash containing glucoamylase and inoculated with yeast is used for this example. Three 3-liter fermentations are conducted at 36° C. for 60 hours. The amounts of AFP added to the mash is 0 for the control, 10 and 20 SAPU (moles of tyrosin produced per minute) per liter of mash. After the fermentation, alcohol is recovered by distillation. The stillage is filtered through a course filter to separate the spent grain (cake) and thin stillage (filtrate). The resulting filtrate is then concentrated to 50% DS. The viscosity is then measured as in Example 9. The viscosity of the control syrup is 503 cp and that for 10 and 20 units of AFP per liter of mash is 233 and 197 cp respectively. These results show that the action of the protease in the fermenter does reduce the viscosity of the thin stillage.

EXAMPLE 11

Presumably, the protease (AFP) effects the fermentation by hydrolyzing protein and thereby increasing the amino nitrogen i.e. peptides of various lengths and amino acids. AFP-2000 is a commercial protease obtained by a controlled fermentation of *Aspergillus niger* var. This protease is characterized by its ability to hydrolyze proteins under acid conditions. AFP requires no activator or cofactors for complete activity expression. The assay for this enzyme (a copy of which can be obtained from Solvay Enzymes, Inc.) is the digestion of casein. It follows then that other proteases that are active in the pH range of the ethanol proteases that are active in the pH range of the ethanol fermentation may show results similar to AFP. If other proteases do not show benefit similar to AFP then AFP would seem to contain a very specific reactivity with respect to ethanol yield in fermentation found in fermentation. To test this hypothesis other proteases were assayed under the same AFP to conditions as measure the SAPU value i.e. moles of tyrosin produce per minute, under the conditions of the assay. Table 11 lists the proteases tested. Liquefied whole corn mash was simultaneously saccharified and fermented in the presence of these proteases, adding equal SAPU activities for each protease.

Whole ground corn was liquefied as described in Example 1. The fermentation flasks were prepared as in Example 1 except the mash DS was adjust to 27.76% DS w/w. The AG (Distillase L-200) and the equivalent 4.8 SAPU of protease were added. The fermentation was carried out in 33° C. water. Sampling and analysis of the samples were conducted similar to the procedure given in Example 1. A summary of the ethanol levels are given in Table 12 for the various proteases tested. All the proteases tested did show an improvement in ethanol formation rate relative to the control. Some of the proteases tested showed a higher fermentation rate than at the same SAPU level. This may be due to the fact that SAPU is not always the best characteristic by which to quantify a protease in terms of increasing yeast fermentation.

TABLE 1

Influence of AFP on the simultaneous saccharification/fermentation of whole corn mash.

| Fermentation Time (Hrs) | pH | Glucose % w/v | Maltose % w/v | Non-Ferm Carb % w/v | Ethanol % w/v | Glycerol % w/v |
|---|---|---|---|---|---|---|
| Flask 1 - 0.12 ml AG, 0 ml AFP ||||||| 
| 3 | 4.6 | 2.38 | 1.36 | 16.38 | 1.01 | .21 |
| 17 | 3.9 | 4.92 | 2.67 | 4.68 | 5.30 | .63 |
| 41 | 3.7 | 3.30 | .18 | 1.65 | 10.40 | .98 |
| 65 | 3.8 | 2.21 | .23 | .47 | 12.00 | 1.05 |
| 95 | 3.9 | 2.07 | .23 | .35 | 12.15 | 1.01 |
| Flask 2 - 0.12 ml AG, .1 ml AFP ||||||| 
| 3 | 4.6 | 2.70 | 1.47 | 16.25 | 1.02 | .21 |
| 17 | 3.9 | 3.21 | 2.10 | 4.57 | 7.27 | .68 |
| 41 | 3.9 | .63 | .19 | .78 | 12.87 | .98 |
| 65 | 4.0 | .39 | .23 | .34 | 13.47 | .98 |
| 95 | 4.1 | .58 | .21 | .38 | 13.52 | .97 |
| Flask 3 - 0.12 ml AG, .3 ml AFP ||||||| 
| 3 | 4.6 | 2.72 | 1.43 | 15.30 | .97 | .20 |
| 17 | 3.9 | 2.41 | 1.25 | 4.33 | 8.51 | .68 |
| 41 | 4.0 | .13 | .19 | .59 | 13.44 | .92 |
| 65 | 4.1 | .15 | .20 | .39 | 13.83 | .95 |
| 95 | 4.1 | .43 | .16 | .27 | 13.74 | .92 |
| Flask 4 - 0.16 ml AG, 0 ml AFP ||||||| 
| 3 | 4.6 | 3.96 | 1.68 | 14.74 | .91 | .21 |
| 17 | 3.9 | 7.39 | 1.20 | 3.93 | 5.53 | .67 |
| 41 | 3.7 | 3.97 | .23 | .87 | 10.50 | .95 |
| 65 | 3.8 | 2.40 | .27 | .34 | 12.17 | 1.06 |
| 95 | 3.9 | 2.40 | .26 | .34 | 12.14 | 1.08 |
| Flask 5 - 0.16 ml AG, .1 ml AFP ||||||| 
| 3 | 4.6 | 4.38 | 1.80 | 14.18 | .99 | .21 |
| 17 | 3.9 | 5.12 | .75 | 3.68 | 7.23 | .71 |
| 41 | 3.9 | .83 | .21 | .50 | 12.98 | 1.02 |
| 65 | 4.0 | .71 | .26 | .34 | 13.41 | 1.00 |
| 95 | 4.1 | .79 | .23 | .37 | 13.59 | 1.02 |
| Flask 6 - 0.12 ml AG, .3 ml AFP ||||||| 
| 3 | 4.6 | 4.72 | 1.91 | 13.37 | 1.07 | .21 |
| 17 | 4.0 | 4.05 | .44 | 3.41 | 8.67 | .73 |
| 41 | 4.0 | .07 | .20 | .41 | 13.68 | .96 |
| 65 | 4.1 | .19 | .19 | .29 | 13.77 | .96 |
| 95 | 4.2 | .54 | .21 | .42 | 13.90 | .94 |
| Flask 7 - 0.20 ml AG, 0 ml AFP ||||||| 
| 3 | 4.7 | 6.19 | 2.26 | 11.41 | .96 | .21 |
| 17 | 3.9 | 9.18 | .30 | 2.68 | 5.68 | .69 |
| 41 | 3.7 | 4.14 | .19 | .64 | 10.61 | .98 |
| 65 | 3.9 | 2.56 | .27 | .31 | 11.98 | 1.08 |
| 95 | 3.9 | 2.59 | .26 | .33 | 12.07 | 1.05 |
| Flask 8 - 0.20 ml AG, .1 ml AFP ||||||| 
| 3 | 4.6 | 6.79 | 2.44 | 10.63 | .94 | .20 |
| 17 | 4.0 | 6.87 | .27 | 2.41 | 7.53 | .75 |
| 41 | 4.0 | .74 | .26 | .36 | 13.00 | 1.01 |
| 65 | 4.0 | .58 | .26 | .36 | 13.56 | 1.05 |
| 95 | 4.1 | .82 | .21 | .30 | 13.57 | 1.04 |
| Flask 9 - 0.20 ml AG, .3 ml AFP ||||||| 
| 3 | 4.7 | 7.05 | 2.58 | 10.27 | 1.03 | .20 |
| 17 | 4.0 | 5.26 | .21 | 2.34 | 8.68 | .75 |
| 41 | 4.0 | .07 | .23 | .38 | 13.61 | .90 |
| 65 | 4.1 | .31 | .22 | .40 | 13.86 | 1.00 |
| 95 | 4.1 | .52 | .21 | .42 | 13.89 | .97 |

TABLE 1-continued

Influence of AFP on the simultaneous saccharification/fermentation of whole corn mash.

| Fermentation Time (Hrs) | pH | HPLC Profile | | | | |
|---|---|---|---|---|---|---|
| | | Glucose % w/v | Maltose % w/v | Non-Ferm Carb % w/v | Ethanol % w/v | Glycerol % w/v |
| Flask 10 - 0.25 ml AG, 0 ml AFP | | | | | | |
| 3 | 4.6 | 8.48 | 3.20 | 7.59 | .96 | .20 |
| 17 | 3.9 | 10.19 | .19 | 1.86 | 5.77 | .72 |
| 41 | 3.8 | 4.07 | .24 | .41 | 10.81 | 1.04 |
| 65 | 3.9 | 2.62 | .27 | .33 | 11.93 | 1.11 |
| 95 | 4.0 | 2.78 | .29 | .34 | 12.20 | 1.06 |
| Flask 11 - 0.25 ml AG, .1 ml AFP | | | | | | |
| 3 | 4.6 | 5.99 | 2.12 | 11.49 | 1.01 | .20 |
| 17 | 4.0 | 7.76 | .17 | 1.59 | 7.44 | .77 |
| 41 | 4.0 | .88 | .27 | .34 | 13.10 | 1.01 |
| 65 | 4.1 | .90 | .26 | .36 | 13.51 | 1.05 |
| 95 | 4.2 | 1.02 | .22 | .32 | 13.42 | 1.01 |
| Flask 12 - 0.25 ml AG, .3 ml AFP | | | | | | |
| 3 | 4.6 | 6.33 | 2.30 | 10.43 | 1.02 | .20 |
| 17 | 4.0 | 5.97 | .17 | 1.48 | 8.75 | .80 |
| 41 | 4.0 | .07 | .22 | .36 | 13.59 | .97 |
| 65 | 4.1 | .23 | .19 | .37 | 13.82 | 1.01 |
| 95 | 4.2 | .49 | .18 | .36 | 13.91 | .97 |

Each flask (500 Erlenmeyer) contained 450 gm liquefied whole corn mash and the indicated amounts of Distillase L-200 (AG) and 2% AFP-2000 (acid fungal protease). Flasks placed in 36° C. water bath.

TABLE 2

Influence of varying levels of AFP on the simultaneous saccharification/fermentation of whole corn mash at two yeast inoculation levels.

| Fermentation Time (Hrs) | pH | HPLC Profile | | | | |
|---|---|---|---|---|---|---|
| | | Glucose % w/v | Maltose % w/v | Non-Ferm Carb % w/v | Ethanol % w/v | Glycerol % w/v |
| Flask 1 - 0.12 ml AG, 0. ml AFP, .8 gm yeast | | | | | | |
| 3 | 4.8 | 3.37 | 1.40 | 15.63 | .96 | .21 |
| 15 | 4.1 | 3.90 | 3.42 | 5.81 | 4.69 | .59 |
| 39 | 3.9 | 3.10 | .29 | 1.85 | 9.94 | .95 |
| 64 | 4.0 | 2.05 | .38 | .51 | 12.18 | 1.05 |
| 89 | 4.1 | 2.04 | .38 | .38 | 12.15 | 1.02 |
| Flask 2 - 0.12 ml AG, 0.05 ml AFP, .8 gm yeast | | | | | | |
| 3 | 4.8 | 3.49 | 1.40 | 15.37 | .92 | .20 |
| 15 | 4.1 | 3.02 | 3.27 | 5.67 | 5.11 | .60 |
| 39 | 4.0 | 1.28 | .27 | 1.55 | 11.16 | .93 |
| 64 | 4.1 | .85 | .35 | .47 | 13.22 | 1.01 |
| 89 | 4.2 | .87 | .39 | .43 | 13.06 | 1.01 |
| Flask 3 - 0.12 ml AG, 0.10 ml AFP, .8 gm yeast | | | | | | |
| 3 | 4.8 | 3.79 | 1.45 | 14.87 | .95 | .20 |
| 15 | 4.1 | 2.62 | 3.29 | 5.66 | 5.82 | .61 |
| 39 | 4.1 | .88 | .33 | 1.25 | 11.82 | .93 |
| 64 | 4.1 | .53 | .37 | .45 | 13.56 | 1.00 |
| 89 | 4.3 | .42 | .29 | .34 | 13.35 | .98 |
| Flask 4 - 0.12 ml AG, 0.25 ml AFP, .8 gm yeast | | | | | | |
| 3 | 4.8 | 4.05 | 1.52 | 15.19 | 1.01 | .20 |
| 15 | 4.1 | 1.69 | 3.01 | 5.60 | 6.63 | .60 |
| 39 | 4.1 | .52 | .30 | .94 | 12.40 | .92 |
| 64 | 4.2 | .12 | .32 | .46 | 13.68 | .94 |
| 89 | 4.3 | .19 | .25 | .36 | 13.04 | .91 |
| Flask 5 - 0.12 ml AG, 0. ml AFP, 1.6 gm yeast | | | | | | |
| 3 | 4.7 | 3.50 | 1.55 | 14.54 | 2.45 | .28 |
| 15 | 4.0 | 1.91 | 3.27 | 5.63 | 6.31 | .71 |
| 39 | 4.0 | 1.65 | .36 | 1.42 | 11.30 | 1.03 |
| 64 | 4.0 | 2.43 | .48 | .49 | 11.77 | 1.03 |
| 89 | 4.1 | 2.50 | .44 | .38 | 11.97 | .99 |
| Flask 6 - 0.12 ml AG, 0.05 ml AFP, 1.6 gm yeast | | | | | | |
| 3 | 4.7 | 3.68 | 1.58 | 14.67 | 1.50 | .28 |
| 15 | 4.0 | 1.34 | 2.99 | 5.52 | 6.66 | .69 |
| 39 | 4.1 | .91 | .30 | 1.16 | 11.79 | .95 |
| 64 | 4.1 | 1.68 | .40 | .45 | 11.53 | .97 |
| 89 | 4.2 | 1.62 | .38 | .38 | 12.50 | .95 |
| Flask 7 - 0.12 ml AG, 0.10 ml AFP, 1.6 gm yeast | | | | | | |
| 3 | 4.7 | 3.84 | 1.64 | 14.01 | 1.63 | .29 |
| 15 | 4.0 | .07 | 1.25 | 7.40 | 7.13 | .69 |
| 39 | 4.2 | .70 | .35 | .85 | 11.99 | .91 |
| 64 | 4.1 | 1.12 | .29 | .35 | 11.44 | .86 |
| 89 | 4.2 | 1.22 | .31 | .35 | 12.68 | .93 |
| Flask 8 - 0.12 ml AG, 0.25 ml AFP, 1.6 gm yeast | | | | | | |

TABLE 2-continued

Influence of varying levels of AFP on the simultaneous saccharification/fermentation of whole corn mash at two yeast inoculation levels.

| Fermentation Time (Hrs) | pH | Glucose % w/v | Maltose % w/v | Non-Ferm Carb % w/v | Ethanol % w/v | Glycerol % w/v |
|---|---|---|---|---|---|---|
| 3 | 4.6 | 3.82 | 1.65 | 13.77 | 1.66 | .28 |
| 15 | 4.0 | .07 | 1.31 | 6.52 | 7.89 | .69 |
| 39 | 4.2 | .61 | .32 | .68 | 12.34 | .87 |
| 64 | 4.2 | .95 | .28 | .40 | 12.97 | .90 |
| 89 | 4.3 | 1.08 | .02 | .36 | 13.07 | .89 |

Each flask contained 450 gm liquefied whole corn mash and the indicated level of Distillase, 2% AFP and dry Fleishmann's yeast. Flasks were placed in 36° C. water bath.

TABLE 3

Influence of yeast extract on the simultaneous saccharification/fermentation of liquefied whole corn mash.

| Flask | $AG^a$ (ml) | $AFP^b$ (ml) | $YE^c$ (ml) | Dry $Yeast^d$ (gm) | Ethanol Level % v/v Fermentation Time (Hrs.) | | | | |
|---|---|---|---|---|---|---|---|---|---|
| | | | | | 3 | 17 | 41 | 65 | 93 |
| 1 | .12 | 0 | 0 | .8 | .66 | 3.28 | 7.72 | 9.95 | 11.52 |
| 2 | .12 | .1 | 0 | .8 | .67 | 4.78 | 10.81 | 12.53 | 11.87 |
| 3 | .12 | 0 | 2 | .8 | .58 | 4.06 | 9.47 | 11.75 | 12.17 |
| 4 | .12 | .1 | 2 | .8 | .81 | 5.34 | 11.41 | 12.73 | 12.57 |
| 5 | .12 | 0 | 4 | .8 | .75 | 4.20 | 10.43 | 12.67 | 12.36 |
| 6 | .12 | .1 | 4 | .8 | .74 | 5.95 | 11.81 | 12.74 | 12.69 |
| 7 | .12 | 0 | 10 | .8 | .58 | 5.87 | 12.08 | 12.87 | 11.91 |
| 8 | .12 | .1 | 10 | .8 | .65 | 7.11 | 12.25 | 12.61 | 12.36 |
| 9 | .12 | 0 | 16 | .8 | .82 | 7.65 | 12.23 | 12.23 | 12.36 |
| 10 | .12 | .1 | 16 | .8 | .59 | 7.77 | 12.23 | 12.30 | 12.11 |

$^a$AG = volume of Diazyme L-200
$^b$AFP = volume of a 2% solution of acid fungal protease
$^c$YE = volume of a 20% solution of Amberex 1003
$^d$Dry Yeast = amount of Fleischmann's dry bakers yeast.
Each flask contained 450 gm of liquefied whole corn mash. Flasks were placed in 33° C. water bath.

TABLE 4

Simultaneous Saccharification/Fermentation of Commercial Whole Corn Liquified Mash Containing Backset

| Flask | $AFP^a$ (ml) | Ethanol Level % v/v Fermentation Time (Hrs) | | | |
|---|---|---|---|---|---|
| | | 2.5 | 19.5 | 43.5 | 67 |
| 1 | 0 | 2.14 | 5.91 | 11.13 | 11.07 |
| 2 | .05 | 2.12 | 7.32 | 11.96 | 13.26 |
| 3 | .10 | 2.18 | 7.41 | 12.60 | 13.89 |

$^a$AFP = volume of a 2% solution AFT-2000.
Each flask contained 450 gm of mash. Fermentation carried out at 30° C.

TABLE 5

Influence of AFP on the simultaneous saccharification/fermentation of whole corn mash at varous solids.

| Fermentation Time (Hrs) | pH | Glucose % w/v | Maltose % w/v | Non-Carb % w/v | Ethanol % w/v | Lactic % w/v | Glycerol % w/v |
|---|---|---|---|---|---|---|---|
| Flask 1 - 23.7% w/w Mash DS, 0.12 ml $AG^a$, 0 ml $AFP^b$ | | | | | | | |
| 3 | 4.5 | 2.14 | 3.12 | 12.06 | .83 | .18 | .14 |
| 16 | 3.9 | 2.72 | 5.93 | 4.46 | 4.41 | .18 | .52 |
| 40 | 3.8 | .94 | 1.71 | 3.43 | 9.13 | .19 | .84 |
| 64 | 3.9 | .56 | .10 | 1.06 | 12.13 | .22 | 1.03 |
| 88 | 3.8 | ND | .09 | .38 | 12.94 | .19 | 1.03 |
| Flask 2 - 23.7% w/w Mash DS, 0.12 ml AG, 0.10 ml AFP | | | | | | | |
| 3 | 4.4 | 2.28 | 3.17 | 11.49 | .83 | .71 | .13 |
| 16 | 3.9 | 1.90 | 5.71 | 4.16 | 5.18 | .18 | .54 |
| 40 | 3.7 | .28 | .46 | 2.87 | 10.55 | .19 | .82 |
| 64 | 4.0 | ND | .08 | .74 | 12.84 | .21 | .93 |
| 88 | 3.9 | ND | .06 | .39 | 12.95 | .19 | .91 |
| Flask 3 - 26.4% w/w Mash DS, 0.132 ml AG, 0 ml AFP | | | | | | | |
| 3 | 4.4 | 2.24 | 3.49 | 14.16 | .95 | .19 | .15 |
| 16 | 4.0 | 3.43 | 6.65 | 5.03 | 4.74 | .20 | .56 |
| 40 | 3.8 | 1.37 | 2.16 | 3.97 | 9.73 | .20 | .89 |
| 64 | 4.0 | 1.48 | .11 | 1.44 | 12.74 | .21 | 1.06 |
| 88 | 3.9 | .59 | .16 | .60 | 13.04 | .20 | 1.04 |
| Flask 4 - 26.4% w/w Mash DS, 0.132 ml AG, .11 ml AFP | | | | | | | |
| 3 | 4.4 | 2.17 | 3.08 | 11.51 | .81 | .17 | .13 |

TABLE 5-continued

Influence of AFP on the simultaneous saccharification/fermentation of whole corn mash at varous solids.

| Fermentation[1] Time (Hrs) | pH | HPLC Profile | | | | | |
|---|---|---|---|---|---|---|---|
| | | Glucose % w/v | Maltose % w/v | Non-Carb % w/v | Ethanol % w/v | Lactic % w/v | Glycerol % w/v |
| 16 | 4.0 | 2.55 | 6.14 | 4.60 | 5.60 | .20 | .58 |
| 40 | 3.9 | .58 | 1.00 | 3.62 | 11.39 | .21 | .89 |
| 64 | 4.1 | ND | .10 | .87 | 14.17 | .21 | 1.02 |
| 88 | 4.0 | ND | .08 | .41 | 13.98 | .20 | .98 |
| Flask 5 - 28.3% w/w Mash DS, 0.144 ml AG, 0 ml AFP | | | | | | | |
| 3 | 4.4 | 2.62 | 3.48 | 12.84 | .87 | .18 | .14 |
| 16 | 3.9 | 3.88 | 6.42 | 4.80 | 4.67 | .20 | .53 |
| 40 | 3.9 | 2.31 | 1.93 | 4.12 | 10.15 | .21 | .91 |
| 64 | 4.2 | 2.74 | .16 | 1.57 | 13.20 | .22 | 1.09 |
| 88 | 3.9 | 2.19 | .20 | .79 | 13.77 | .21 | 1.10 |
| Flask 6 - 28.3% w/w Mash DS, 0.144 ml AG, 0.12 ml AFP | | | | | | | |
| 3 | 4.3 | 3.24 | 4.14 | 14.02 | 1.02 | .20 | .16 |
| 16 | 3.9 | 2.95 | 5.67 | 4.40 | 5.18 | .19 | .54 |
| 40 | 3.9 | .74 | 1.20 | 3.90 | 11.84 | .21 | .92 |
| 64 | 4.2 | .56 | .18 | 1.06 | 15.00 | .22 | 1.10 |
| 88 | 4.0 | .40 | .18 | .42 | 15.30 | .22 | 1.11 |
| Flask 7 - 30.6% w/w Mash DS, 0.156 ml AG, 0 ml AFP | | | | | | | |
| 3 | 4.4 | 3.96 | 4.82 | 15.92 | 1.15 | .22 | .18 |
| 16 | 4.0 | 4.65 | 6.73 | 5.12 | 4.74 | .21 | .54 |
| 40 | 3.9 | 3.19 | 2.40 | 4.66 | 10.35 | .22 | .94 |
| 64 | 4.2 | 4.27 | .19 | 2.00 | 13.21 | .23 | 1.11 |
| 88 | 4.1 | 3.59 | .22 | .92 | 12.77 | .21 | 1.05 |
| Flask 8 - 30.6% w/w Mash DS, 0.156 ml AG, 0.13 ml AFP | | | | | | | |
| 3 | 4.4 | 4.36 | 4.94 | 14.14 | 1.12 | .13 | .17 |
| 16 | 4.0 | 3.78 | 6.10 | 4.91 | 5.76 | .21 | .57 |
| 40 | 4.0 | 1.37 | 1.24 | 4.16 | 12.35 | .23 | .93 |
| 64 | 4.3 | 2.16 | .23 | 1.32 | 15.09 | .24 | 1.08 |
| 88 | 4.1 | 2.13 | .23 | .63 | 15.59 | .21 | .98 |
| Flask 9 - 32.8% w/w Mash DS, 0.168 ml AG, 0 ml AFP | | | | | | | |
| 3 | 4.5 | 5.32 | 5.61 | 15.18 | 1.18 | .24 | .19 |
| 16 | 4.0 | 5.68 | 7.07 | 5.54 | 4.94 | .22 | .59 |
| 40 | 4.0 | 4.68 | 2.59 | 5.16 | 10.56 | .24 | 1.01 |
| 64 | 4.3 | 6.28 | .24 | 2.42 | 13.37 | .25 | 1.20 |
| 88 | 4.2 | 5.86 | .27 | 1.26 | 13.14 | .23 | 1.14 |
| Flask 10 - 32.8% w/w Mash DS, 0.168 ml AG, .14 ml AFP | | | | | | | |
| 3 | 4.4 | 5.00 | 5.37 | 14.09 | 1.14 | .22 | .17 |
| 16 | 4.0 | 4.59 | 6.38 | 5.24 | 5.72 | .21 | .60 |
| 40 | 4.0 | 2.63 | 1.57 | 4.75 | 12.73 | .25 | 1.00 |
| 64 | 4.3 | 4.66 | .27 | 1.84 | 14.86 | .26 | 1.15 |
| 88 | 4.3 | 4.75 | .28 | .98 | 14.16 | .24 | 1.06 |

[1]All flasks containing 450 gm mash were inoculated with 0.8 gm of dry Fleishmann's yeast and incubated at 33° C.
[a]AG = volume of Distillase L-200 added per flask.
[b]AFP = volume of a 2% solution of AFP per flask.

TABLE 6

Summary of Ethanol Levels at Various Mash Solids Levels from Table 5.

| Flask | Mash % DS | AFP | Ethanol % v/v | | | | |
|---|---|---|---|---|---|---|---|
| | | | 3 hr | 16 hr | 40 hr | 64 hr | 88 hr |
| 1 | 23.7 | − | .83 | 4.41 | 9.13 | 12.13 | 12.94 |
| 2 | 23.7 | + | .83 | 5.18 | 10.55 | 12.84 | 12.95 |
| 3 | 26.4 | − | .95 | 4.74 | 9.73 | 12.74 | 13.04 |
| 4 | 26.4 | + | .81 | 5.60 | 11.39 | 14.17 | 13.98 |
| 5 | 28.3 | − | .87 | 4.67 | 10.15 | 13.20 | 13.77 |
| 6 | 28.3 | + | 1.02 | 5.18 | 11.84 | 15.00 | 15.30 |
| 7 | 30.6 | − | 1.15 | 4.74 | 10.35 | 13.21 | 12.77 |
| 8 | 30.6 | + | 1.12 | 5.76 | 12.35 | 15.09 | 15.59 |
| 9 | 32.8 | − | 1.18 | 4.94 | 10.56 | 13.37 | 13.14 |
| 10 | 32.8 | + | 1.14 | 5.72 | 12.73 | 14.86 | 14.16 |

TABLE 7

Influence of AFP on the Simultaneous Saccharification/Fermentation of Liquefied Corn Mash Containing Backset.

| Flask[1] | Mash % DS | AG (ml) | AFP (ml) | Ethanol % v/v | | | | |
|---|---|---|---|---|---|---|---|---|
| | | | | 3 hr | 16 hr | 40 hr | 64 hr | 88 hr |
| 1 | 24.2 | .120 | 0 | .88 | 4.68 | 9.82 | 11.83 | 11.65 |
| 2 | 24.2 | .120 | 0.10 | .87 | 5.34 | 11.15 | 12.18 | 11.81 |
| 3 | 26.33 | .132 | 0 | .94 | 4.99 | 10.06 | 12.83 | 11.82 |
| 4 | 26.33 | .132 | 0.11 | .93 | 4.87 | 11.10 | 13.21 | 12.93 |
| 5 | 28.6 | .144 | 0 | .92 | 5.12 | 10.77 | 13.92 | 13.51 |
| 6 | 28.6 | .144 | 0.12 | 1.02 | 5.85 | 12.01 | 14.34 | 13.82 |
| 7 | 31.0 | .156 | 0 | 1.27 | 5.75 | 11.05 | 13.90 | 13.42 |
| 8 | 31.0 | .156 | 0.13 | 1.19 | 5.65 | 11.77 | 15.16 | 14.43 |
| 9 | 32.6 | .168 | 0 | 1.28 | 5.86 | 11.20 | 13.90 | 13.72 |
| 10 | 32.6 | .168 | 0.14 | 1.20 | 6.50 | 12.90 | 15.32 | 14.90 |

[1]All flasks contained 450 gm of mash, inoculated with .8 gm of dry Fleishmann's yeast and incubated at 33° C.

TABLE 8

Fermentation of Whole Corn Mash Saccharified with AFP Saccharified with AFP present at 60° C. prior to Fermentation

| Fermentation Time (Hrs) | pH | HPLC Profile | | | | |
|---|---|---|---|---|---|---|
| | | Glucose % w/v | Maltose % w/v | Non-Ferm Carb % w/v | Ethanol % w/v | Glycerol % w/v |

TABLE 8-continued

| | | Flask 1 - 0.12 ml AG[a], 0 ml AFP[b], 0.8 gm yeast | | | | |
|---|---|---|---|---|---|---|
| 3 | 4.5 | 16.57 | .46 | 1.54 | .69 | .15 |
| 20 | 3.8 | 8.95 | .32 | 1.21 | 5.60 | .78 |
| 44 | 3.9 | 2.96 | .30 | .90 | 16.22 | 1.09 |
| 70 | 4.0 | .05 | .26 | .51 | 12.21 | 1.18 |
| | | Flask 2 - 0.12 ml AG, .10 ml AFP, .8 gm yeast | | | | |
| 3 | 4.4 | 15.64 | .53 | 1.63 | .75 | .16 |
| 20 | 3.7 | 6.17 | .37 | 1.32 | 7.45 | .86 |
| 44 | 4.0 | .04 | .39 | .81 | 12.88 | 1.14 |
| 70 | 4.0 | .01 | .29 | .42 | 12.25 | 1.07 |
| | | Flask 3 - 0.12 ml AG, 12 ml AFP, .8 gm yeast | | | | |
| 3 | 4.4 | 15.78 | .62 | 1.74 | .83 | .16 |
| 20 | 3.8 | 5.65 | .37 | 1.24 | 6.79 | .79 |
| 44 | 4.0 | .04 | .38 | .81 | 12.62 | 1.12 |
| 70 | 4.0 | .02 | .30 | .42 | 12.62 | 1.08 |
| | | Flask 4 - 0.12 ml AG, .15 ml AFP, .8 gm yeast | | | | |
| 3 | 4.4 | 16.51 | .60 | 1.74 | .69 | .15 |
| 20 | 3.8 | 6.04 | .36 | 1.36 | 6.90 | .82 |
| 44 | 4.2 | .04 | .37 | .83 | 12.81 | 1.12 |
| 70 | 4.1 | .01 | .30 | .41 | 12.42 | 1.05 |
| | | Flask 5 - 0.12 ml AG, .20 ml AFP, .8 gm yeast | | | | |
| 3 | 4.5 | 15.80 | .48 | 1.63 | .73 | .15 |
| 20 | 3.8 | 5.81 | .35 | 1.37 | 7.70 | .87 |
| 44 | 4.0 | .03 | .36 | .80 | 12.38 | 1.08 |
| 70 | 4.0 | .02 | .30 | .45 | 12.76 | 1.07 |

[a]AG = volume of Distillase L-200 added per flask.
[b]AFP = volume of a 2% solution of AFP-2000.

Fermentation of Whole Corn Mash Saccharified with AFP
Saccharified at 60° C. prior to Fermentation,
AFP Present During Fermentation

| | | HPLC Profile | | | | |
|---|---|---|---|---|---|---|
| Fermentation Time (Hrs) | pH | Glucose % w/v | Maltose % w/v | Carb % w/v | Ethanol % w/v | Glycerol % w/v |
| | | Flask 6 - 0.12 ml AG[a], .10 ml AFP[b], .8 gm yeast | | | | |
| 3 | 4.4 | 15.70 | .38 | 1.30 | .62 | .14 |
| 20 | 3.8 | 7.60 | .31 | 1.10 | 6.76 | .84 |
| 44 | 4.0 | .09 | .35 | .71 | 12.39 | 1.10 |
| 70 | 4.1 | .02 | .30 | .41 | 12.97 | 1.10 |
| | | Flask 7 - 0.12 ml AG, 12 ml AFP, .8 gm yeast | | | | |
| 3 | 4.4 | 16.08 | .40 | 1.44 | .65 | .14 |
| 20 | 3.7 | 6.69 | .29 | 1.19 | 6.32 | .78 |
| 44 | 4.1 | .04 | .35 | .75 | 12.43 | 1.08 |
| 70 | 4.1 | .02 | .28 | .42 | 12.76 | 1.08 |
| | | Flask 8 - 0.12 ml AG, .15 ml AFP, .8 gm yeast | | | | |
| 3 | 4.4 | 15.49 | .49 | 1.62 | .60 | .14 |
| 20 | 3.8 | 6.41 | .35 | 1.39 | 7.13 | .85 |
| 44 | 4.1 | .61 | .34 | .80 | 12.51 | 1.08 |
| 70 | 4.1 | .02 | .27 | .44 | 12.78 | 1.05 |
| | | Flask 9 - 0.12 ml AG, .20 ml AFP, .8 gm yeast | | | | |
| 3 | 4.4 | 15.84 | .50 | 1.64 | .62 | .14 |
| 20 | 3.8 | 6.05 | .35 | 1.59 | 7.11 | .82 |
| 44 | 4.12 | .04 | .33 | .81 | 12.41 | 1.07 |
| 70 | 4.11 | .03 | .26 | .41 | 12.15 | 1.01 |

[a]AG = volume of Distillase L-2000 added per flask.
[b]AFP = volume of a 2% solution of AFP per flask.

TABLE 9

Summary of Ethanol Levels From Table 8

| AFP | Pre Sacc | Post Sacc | Ethanol % v/v | | | |
|---|---|---|---|---|---|---|
| | | | 3 hrs | 20 hrs | 44 hrs | 70 hrs |
| 0 | — | — | .69 | 5.60 | 10.22 | 12.21 |
| .10 ml | + | — | .75 | 7.45 | 12.88 | 12.25 |
| .10 ml | — | + | .62 | 6.75 | 12.39 | 12.97 |
| .12 ml | + | — | .83 | 6.79 | 12.62 | 12.62 |
| .12 ml | — | + | .65 | 6.32 | 12.43 | 12.76 |
| .15 ml | + | — | .69 | 6.90 | 12.81 | 12.42 |
| .15 ml | — | + | .60 | 7.13 | 12.51 | 12.78 |
| .20 ml | + | — | .73 | 7.70 | 12.38 | 12.76 |
| .20 ml | — | + | .62 | 7.11 | 12.42 | 12.15 |

TABLE 10

Influence of AFP on the simultaneous
saccharification/fermentation of whole milo mash.

| | | HPLC Profile | | | | |
|---|---|---|---|---|---|---|
| Fermentation Time (Hrs) | pH | Glucose % w/v | Maltose % w/v | Non-Ferm Carb % w/v | Ethanol % w/v | Glycerol % w/v |
| | | Flask 1 - 0.12 ml AG, 0 ml AFP, .8 gm yeast | | | | |
| 3 | 4.3 | 2.44 | 1.40 | 15.54 | .84 | .18 |

TABLE 10-continued

Influence of AFP on the simultaneous saccharification/fermentation of whole milo mash.

| Fermentation Time (Hrs) | pH | HPLC Profile | | | | |
|---|---|---|---|---|---|---|
| | | Glucose % w/v | Maltose % w/v | Non-Ferm Carb % w/v | Ethanol % w/v | Glycerol % w/v |
| 17 | 3.9 | 1.09 | 3.63 | 8.16 | 5.07 | .61 |
| 41 | 3.7 | 1.06 | .77 | 3.84 | 9.76 | .94 |
| 70 | 3.8 | .10 | .31 | .91 | 11.94 | 1.03 |
| Flask 2 - 0.12 ml AG, 0.1 ml AFP, .8 gm yeast | | | | | | |
| 3 | 4.3 | 2.85 | 1.47 | 15.37 | .85 | .18 |
| 17 | 3.9 | .75 | 3.38 | 7.31 | 5.78 | .58 |
| 41 | 3.8 | .41 | .32 | 2.40 | 11.19 | .86 |
| 70 | 3.8 | .06 | .22 | .70 | 12.58 | .91 |
| Flask 3 - 0.12 ml AG, 0.2 ml AFP, .8 gm yeast | | | | | | |
| 3 | 4.3 | 2.69 | 1.40 | 14.45 | .75 | .17 |
| 17 | 3.9 | .80 | 2.90 | 7.70 | 6.41 | .60 |
| 41 | 3.8 | .19 | .27 | 2.16 | 11.34 | .84 |
| 70 | 3.8 | .06 | .20 | .74 | 12.65 | .87 |

Each flask contained 450 gm liquefied milo mash and the indicated amounts of Distillase L-200 (AG) and 2% AFP-2000. Flasks placed in 33° C. water bath.

TABLE 11

List of Proteases Tested in Example 0-11.

| | | |
|---|---|---|
| *Aspergillus oryzae* | Sigma | Type XXIII: Fungal Protease |
| *Aspergillus saitoi* | Sigma | Type XIII: Funal Protease |
| *Rhizopus* sp. | Sigma | Type XVIII: Fungal Protease |
| Fungal Protease FP - 31,000 | Solvay Enzymes, Inc. | Mixture of acid, neutral and alkaline proteases from *Aspergillus oryzae* var |
| Acid Fungal Protease AFP-2000 (AFP) | Solvay Enzymes, Inc. | Protease from *Aspergillus niger* var. |
| Bromelain | Solvay Enzymes, Inc. | Plant protease mixture isolated from the pineapple plant. |
| Papain | Solvay Enzymes, Inc. | Protease preparation isolated from papaya latex. |

TABLE 12

Influence of Proteases on Simultaneous Saccharification/Fermentation of Whole Corn Mash at 33° C.

| Flask[a] | Protease[b] | Ethanol % v/v | | | |
|---|---|---|---|---|---|
| | | 3 hr | 14 hr | 38 hr | 62 hr |
| 1 | Control | .82 | 3.85 | 8.79 | 11.55 |
| 2 | AFP | .87 | 4.75 | 11.19 | 13.77 |
| 3 | *A. oryzae* | .90 | 6.59 | 13.61 | 14.79 |
| 4 | *A saitoi* | .90 | 6.59 | 13.61 | 14.79 |
| 5 | *Rhizopus* sp. | .92 | 5.04 | 11.11 | 13.46 |
| 6 | FP - 31,000 | .93 | 5.62 | 11.95 | 14.52 |
| 7 | Bromelain | .86 | 6.57 | 13.43 | 14.72 |
| 8 | Papain | .80 | 5.96 | 12.58 | 14.19 |

[a]All flasks contained 450 gm of mash, 0.12 ml Distallase L-200, and 4.8 SAPU of the protease. The flasks were inoculated with 0.8 gm of dry Fleishmann's yeast and placed in 33° C. water bath.
[b]Protease sources given in text for Example 7.

We claim:

1. A process for producing ethanol from raw materials containing a high dry solid mash level having fermentable sugars or constituents which can be converted into sugars, comprising the steps of:
   a. liquefaction of the raw materials in the presence of an alpha amylase to obtain liquefied mash;
   b. saccharification of the liquefied mash in the presence of a glucoamylase to obtain hydrolysed starch and sugars;
   c. fermentation of the hydrolysed starch and sugars by yeast to obtain ethanol; and
   d. recovering the obtained ethanol, wherein an acid fungal protease is introduced to the liquefied mash during the saccharification and/or to the hydrolysed starch and sugars during the fermentation, thereby increasing the rate of production of ethanol as compared to a substantially similar process conducted without the introduction of the protease.

2. The process according to claim 1 wherein the fungal protease is a protease from *Aspergillus niger*.

3. The process according to claim 1 wherein the saccharification and the fermentation steps are carried out simultaneously.

4. The process according to claim 1 wherein the raw materials are whole ground corns, cobs, corns, grains, milo or cereals and their mixtures.

5. The process according to claim 1 wherein the glucoamylase and the acid fungal protease are introduced as a mixture or a composition and used as a single addition.

6. The process according to claim 1 wherein the liquefied mash contains a high dry solids mash level.

7. A composition containing a glucoamylase and an acid fungal protease used in a process according to claim 1.

8. The composition according to claim 7 wherein the glucoamylase is derived from *Aspergillus niger* and the acid fungal protease is derived from *Aspergillus niger*.

9. The process according to claim 1, wherein the total yield of ethanol is increased.

10. The process according to claim 1, wherein the raw materials comprise between 20% and 40% of the high dry solid mash.

11. The process according to claim 1, wherein the raw materials comprise between 25% and 35% of the high dry solid mash.

* * * * *